US006025181A

United States Patent [19]
Onions et al.

[11] Patent Number: 6,025,181
[45] Date of Patent: Feb. 15, 2000

[54] EQUINE HERPESVIRUS-4TK MUTANT

[75] Inventors: David Edward Onions; Lesley Nicolson, both of Glasgow, United Kingdom

[73] Assignees: University Court of the University of Glasgow, Glasgow; Equine Virology Research Foundation, Suffolk, both of United Kingdom

[21] Appl. No.: 08/967,272

[22] Filed: Nov. 7, 1997

Related U.S. Application Data

[62] Continuation of application No. 08/428,277, Apr. 25, 1995, abandoned, which is a continuation of application No. 07/961,673, filed as application No. PCT/GB91/01100, Jul. 5, 1991, abandoned.

[30] Foreign Application Priority Data

Jul. 6, 1990 [GB] United Kingdom .................. 9014951

[51] Int. Cl.$^7$ ............................... C12N 7/00; C12N 7/01; C12N 15/86
[52] U.S. Cl. ..................................... 435/235.1; 435/320.1; 435/325; 424/199.1; 424/205.1; 424/229.1; 424/820
[58] Field of Search ........................... 424/88, 89, 186.1, 424/199.1, 93.2, 94.1, 205.1, 229.1, 820; 435/235, 172.1, 172.3, 173.3, 236, 235.1, 320.1, 325

[56] References Cited

U.S. PATENT DOCUMENTS

| 4,711,850 | 12/1987 | Kit et al. ................................ | 435/235.1 |
| 5,084,271 | 1/1992 | Sheddert ............................... | 424/229.1 |
| 5,223,424 | 6/1993 | Cochran et al. ....................... | 435/236 |
| 5,266,489 | 11/1993 | Rey-Snelonge et al. ............. | 435/320.1 |
| 5,292,653 | 3/1994 | Kit et al. ................................ | 435/235.1 |
| 5,731,188 | 3/1998 | Cochran et al. ....................... | 435/235.1 |

FOREIGN PATENT DOCUMENTS

WO 90/01547  2/1990  WIPO .

OTHER PUBLICATIONS

Nicolson et al, J. Gen. Virol. 71(8):1801–1805, Aug. 1990.
A.A. Cullinane et al., *J. Gen. Virol 69*, 1575–1590 (1988). "Characterization of the genome of equine herpesvirus 1 subtype 2", see discussion.
G.R. Robertson et al. *Nucleic Acids Research*, 16, 11303–11317 (1988). "Evolution of the herpes thymidine kinase: identification and comparison of the equine herpesvirus 1 thymidine kinase gene reveals similarity to a cel-l–encoded thymidylate kinase", see whole article.
J. G. Jacobson; A Conserved Open Reading Frame That Overlaps the Herpes Simplex Virus Thymidine Kinase Gene is Important for Viral Growth in Cell Culture, *J. of Virology* 63:1839–1843 (1989).
Buller et al. 1985. Decreased virulence of recombinant vaccinia virus expression vectors . . . Nature 317:813–15.
Marchioli et al. 1987. A vaccine strain of pseudorabies with deletions in the thymidine kinase . . . Am J. Vet. Res. 48(11):1577–83.
Riggio et al. 1989. Identification and Nucleotide Sequence of the Glycoprotein gB . . . J. of Virol. 63(3):1123–33.
Kit et al. 1985. Attenuated properties of thymidine kinase–negative deletion of . . . Am. J. Vet. Res. 46(6):1359–67.
Nunberg et al. 1989, Identification of the thymidine kinase gene of Feline Herpesvirus . . . J. Virol. 63(8):3240–49.

*Primary Examiner*—Mary E. Mosher
*Attorney, Agent, or Firm*—Alston & Bird LLP

[57] ABSTRACT

An Equine herpesvirus-4 (EHV-4) mutant which does not produce a functional thymidine kinase due to a deletion and/or insertion in the gene encoding thymidine kinase, the deletion and/or insertion made at a position within the thymidine kinase gene such as to not substantially alter expression of the UL24 gene. Recombinant DNA comprising DNA of the EHV-4 mutant, host cells containing the recombinant DNA, and a process for the preparation of the EHV-4 mutant.

15 Claims, 4 Drawing Sheets

```
                        SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
         (A) LENGTH: 1261 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: CDS
         (B) LOCATION: 109..1164

(xi) SEQUENCE DESCRIPTION: SEQ ID NO:1:

CCAAATCTTG AACCATTGCG TTATAGAAGC GGTTGTGGCA CCGTATACCC GCTCTGAGTC         60

TGCTTCTAGC GGTGAGACGC TGTTTACGTT TCATCTCCAC AGGCAGTA ATG GCT GCT        117
                                                   Met Ala Ala
                                                     1

TGC GTA CCC CCG GGA GAA GCT CCA CGA AGC GCC AGC GGA ACG CCC ACC        165
Cys Val Pro Pro Gly Glu Ala Pro Arg Ser Ala Ser Gly Thr Pro Thr
  5                  10                  15

CGG CGG CAA GTA ACA ATA GTT AGA ATT TAC CTC GAT GGA GTT TAT GGC        213
Arg Arg Gln Val Thr Ile Val Arg Ile Tyr Leu Asp Gly Val Tyr Gly
 20                  25                  30                  35

ATC GGT AAG AGC ACG ACG GGA CGA GTT ATG GCA TCG GCT GCT AGC GGA        261
Ile Gly Lys Ser Thr Thr Gly Arg Val Met Ala Ser Ala Ala Ser Gly
                 40                  45                  50

GGA AGT CCA ACT CTA TAC TTT CCA GAG CCT ATG GCG TAC TGG CGG ACT        309
Gly Ser Pro Thr Leu Tyr Phe Pro Glu Pro Met Ala Tyr Trp Arg Thr
             55                  60                  65

CTT TTT GAA ACG GAC GTA ATT AGT GGT ATT TAC GAC ACC CAA AAC CGG        357
Leu Phe Glu Thr Asp Val Ile Ser Gly Ile Tyr Asp Thr Gln Asn Arg
         70                  75                  80

AAA CAG CAG GGA AAT TTG GCC GTT GAT GAC GCG GCA TTA ATA ACT GCG        405
Lys Gln Gln Gly Asn Leu Ala Val Asp Asp Ala Ala Leu Ile Thr Ala
     85                  90                  95
```

```
CAT TAC CAA AGC CGC TTT ACC ACG CCC TAC CTG ATA CTC CAC GAT CAC        453
His Tyr Gln Ser Arg Phe Thr Thr Pro Tyr Leu Ile Leu His Asp His
100                 105                 110                 115

ACT TGT ACG TTG TTT GGG GGA AAC AGC CTA CAG CGT GGA ACA CAA CCG        501
Thr Cys Thr Leu Phe Gly Gly Asn Ser Leu Gln Arg Gly Thr Gln Pro
                120                 125                 130

GAC CTG ACC CTT GTG TTT GAC CGC CAC CCG GTC GCC TCT ACC GTA TGC        549
Asp Leu Thr Leu Val Phe Asp Arg His Pro Val Ala Ser Thr Val Cys
            135                 140                 145

TTT CCA GCA GCC CGC TAC CTA CTC GGT GAC ATG TCA ATG TGC GCG CTA        597
Phe Pro Ala Ala Arg Tyr Leu Leu Gly Asp Met Ser Met Cys Ala Leu
        150                 155                 160

ATG GCT ATG GTT GCT ACT CTA CCA AGA GAA CCC CAG GGT GGT AAC ATT        645
Met Ala Met Val Ala Thr Leu Pro Arg Glu Pro Gln Gly Gly Asn Ile
    165                 170                 175

GTG GTT ACC ACC CTA AAT GTA GAG GAG CAT ATA CGG AGA CTG CGT ACG        693
Val Val Thr Thr Leu Asn Val Glu Glu His Ile Arg Arg Leu Arg Thr
180                 185                 190                 195

CGG GCT AGA ATA GGA GAA CAA ATT GAC ATT ACG CTG ATT GCT ACA TTG        741
Arg Ala Arg Ile Gly Glu Gln Ile Asp Ile Thr Leu Ile Ala Thr Leu
                200                 205                 210

CGA AAT GTG TAC TTT ATG CTA GTT AAT ACA TGT CAC TTT TTG CGC TCT        789
Arg Asn Val Tyr Phe Met Leu Val Asn Thr Cys His Phe Leu Arg Ser
            215                 220                 225

GGG CGA GTT TGG CGC GAC GGT TGG GGT GAG CTA CCC ACT TCC TGT GGG        837
Gly Arg Val Trp Arg Asp Gly Trp Gly Glu Leu Pro Thr Ser Cys Gly
        230                 235                 240

GCT TAT AAG CAT CGC GCC ACA CAG ATG GAC GCC TTC CAA GAG CGC GTT        885
Ala Tyr Lys His Arg Ala Thr Gln Met Asp Ala Phe Gln Glu Arg Val
    245                 250                 255

TCA CCG GAG CTG GGC GAC ACT CTG TTT GCC CTG TTT AAA ACT CAA GAA        933
Ser Pro Glu Leu Gly Asp Thr Leu Phe Ala Leu Phe Lys Thr Gln Glu
260                 265                 270                 275

CTG CTA GAC GAT CGC GGT GTA ATA TTG GAA GTT CAC GCT TGG GCG TTG        981
Leu Leu Asp Asp Arg Gly Val Ile Leu Glu Val His Ala Trp Ala Leu
                280                 285                 290

GAC GCG CTT ATG CTA AAA CTG CGT AAC CTG AAT GTT TTC AGT GCC GAT       1029
Asp Ala Leu Met Leu Lys Leu Arg Asn Leu Asn Val Phe Ser Ala Asp
            295                 300                 305

TTA AGT GGT ACA CCG CGA CAA TGT GCA GCT GTT GTA GAG TCT TTG CTG       1077
Leu Ser Gly Thr Pro Arg Gln Cys Ala Ala Val Val Glu Ser Leu Leu
        310                 315                 320

CCA CTT ATG AGC AGC ACC TTA TCA GAT TTT GAT TCC GCC TCT GCT TTA       1125
Pro Leu Met Ser Ser Thr Leu Ser Asp Phe Asp Ser Ala Ser Ala Leu
    325                 330                 335

GAG CGG GCG GCA CGC ACC TTT AAC GCG GAG ATG GGC GTC TGAAGCTATA        1174
Glu Arg Ala Ala Arg Thr Phe Asn Ala Glu Met Gly Val
340                 345                 350

TGTAATGTTT GTTGTGCCAA TGCCAAAATT GTGAAATAAA GATTCATTTG CCAATATCCA     1234

TCATAGCGCC TTGTGTGTTT CGTGTGT                                        1261

(2) INFORMATION FOR SEQ ID NO:2:

(i) SEQUENCE CHARACTERISTICS:
        (A) LENGTH: 352 amino acids
        (B) TYPE: amino acid
        (D) TOPOLOGY: linear (ii) MOLECULE TYPE: protein
```

(xi) SEQUENCE DESCRIPTION: SEQ ID NO:2:

```
Met Ala Ala Cys Val Pro Pro Gly Glu Ala Pro Arg Ser Ala Ser Gly
 1               5                  10                  15

Thr Pro Thr Arg Arg Gln Val Thr Ile Val Arg Ile Tyr Leu Asp Gly
                20                  25                  30

Val Tyr Gly Ile Gly Lys Ser Thr Thr Gly Arg Val Met Ala Ser Ala
            35                  40                  45

Ala Ser Gly Gly Ser Pro Thr Leu Tyr Phe Pro Glu Pro Met Ala Tyr
        50                  55                  60

Trp Arg Thr Leu Phe Glu Thr Asp Val Ile Ser Gly Ile Tyr Asp Thr
 65                  70                  75                  80

Gln Asn Arg Lys Gln Gln Gly Asn Leu Ala Val Asp Asp Ala Ala Leu
                85                  90                  95

Ile Thr Ala His Tyr Gln Ser Arg Phe Thr Thr Pro Tyr Leu Ile Leu
            100                 105                 110

His Asp His Thr Cys Thr Leu Phe Gly Gly Asn Ser Leu Gln Arg Gly
        115                 120                 125

Thr Gln Pro Asp Leu Thr Leu Val Phe Asp Arg His Pro Val Ala Ser
    130                 135                 140

Thr Val Cys Phe Pro Ala Ala Arg Tyr Leu Leu Gly Asp Met Ser Met
145                 150                 155                 160

Cys Ala Leu Met Ala Met Val Ala Thr Leu Pro Arg Glu Pro Gln Gly
                165                 170                 175

Gly Asn Ile Val Val Thr Thr Leu Asn Val Glu Glu His Ile Arg Arg
            180                 185                 190

Leu Arg Thr Arg Ala Arg Ile Gly Glu Gln Ile Asp Ile Thr Leu Ile
        195                 200                 205

Ala Thr Leu Arg Asn Val Tyr Phe Met Leu Val Asn Thr Cys His Phe
    210                 215                 220

Leu Arg Ser Gly Arg Val Trp Arg Asp Gly Trp Gly Glu Leu Pro Thr
225                 230                 235                 240

Ser Cys Gly Ala Tyr Lys His Arg Ala Thr Gln Met Asp Ala Phe Gln
                245                 250                 255

Glu Arg Val Ser Pro Glu Leu Gly Asp Thr Leu Phe Ala Leu Phe Lys
            260                 265                 270

Thr Gln Glu Leu Leu Asp Asp Arg Gly Val Ile Leu Glu Val His Ala
        275                 280                 285

Trp Ala Leu Asp Ala Leu Met Leu Lys Leu Arg Asn Leu Asn Val Phe
    290                 295                 300

Ser Ala Asp Leu Ser Gly Thr Pro Arg Gln Cys Ala Ala Val Val Glu
305                 310                 315                 320

Ser Leu Leu Pro Leu Met Ser Ser Thr Leu Ser Asp Phe Asp Ser Ala
                325                 330                 335

Ser Ala Leu Glu Arg Ala Ala Arg Thr Phe Asn Ala Glu Met Gly Val
            340                 345                 350
```

(2) INFORMATION FOR SEQ ID NO:3:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

-continued

```
(xi) SEQUENCE DESCRIPTION: SEQ ID NO:3:

GCGGATCGAT AGATCTGCGG CCGCTGCGTT AGTGGTGTT                                    39

(2) INFORMATION FOR SEQ ID NO:4:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

GAGCTCGATA TCTCTAGAGT AGGGCGTGGT AAAGC                                        35

(2) INFORMATION FOR SEQ ID NO:5:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

TCTAGAGATA TCGAGCTCAT ATTGGAAGTT CACGC                                        35

(2) INFORMATION FOR SEQ ID NO:6:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

CCGGGATCCA GATCTGCGGC CGCTCAGAAG ATGTGTACGA                                   40
```

EQUINE HERPESVIRUS-4TK MUTANT

The present application, Ser. No. 08/967,272 is a File Wrapper Continuation of application Ser. NO. 08/428,277, filed Apr. 25, 1995 (now abandoned), which was a continuation of Ser. No. 07/961,673 (now abandoned), filed Feb. 25, 1993 as the national phase filing of PCT/GB91/01100, filed Jul. 5, 1991 which claims the priority date of the British priority document 9014951.9, which is Jul. 6, 1990.

BACKGROUND OF THE INVENTION

The present invention is concerned with an Equine herpesvirus-4 mutant (EHV-4), a recombinant DNA molecule comprising EHV-4 DNA, host cell containing said recombinant DNA molecule, process for the preparation of said EHV-4 mutant, cell culture infected with the EHV-4 mutant, a vaccine derived from the EHV-4 mutant as well as a process for the preparation of such a vaccine.

Equine herpesvirus-4 (EHV-4) is, like the related Equine herpesvirus-1, an alphaherpesvirus responsible for significant economic losses within the equine industry. EHV-4 is primarily associated with respiratory disease though EHV-4 induced abortions are occasionally reported.

The genome of EHV-4 has been characterized as a double-stranded linear DNA molecule consisting of two covalently linked segments (L, 109 kbp; S, 35 kbp) the latter being flanked by inverted repeats.

Control by vaccination of EHV-4 infection has been a long-sought goal.

Current vaccines comprise chemically inactivated virus vaccines and modified live-virus vaccines. However, inactivated vaccines generally induce only a low level of immunity, requiring additional immunizations, disadvantageously require adjuvants and are expensive to produce. Further, some infectious virus particles may survive the inactivation process and causes disease after administration to the animal.

In general, attenuated live virus vaccines are preferred because they evoke a more long-lasting immune response (often both humoral and cellular) and are easier to produce.

Up to now only live attenuated, EHV-4 vaccines are available which are based on live EHV-4 viruses attenuated by serial passages of virulent strains in tissue culture. However, because of this treatment uncontrolled mutations are introduced into the viral genome, resulting in a population of virus particles heterogeneous in their virulence and immunizing properties. In addition it is well known that such traditional attenuated live virus vaccines can revert to virulence resulting in disease of the inoculated animals and the possible spread of the pathogen to other animals. Furthermore, with the existing live attenuated EHV-4 vaccines a positive serological test is obtained for EHV-4 infection. Thus, with the existing EHV-4 vaccines, it is not possible to determine by a (serological) test, e.g. an Elisa, whether a specific animal is a (latent) carrier of the virulent virus or is vaccinated.

Figure 1:
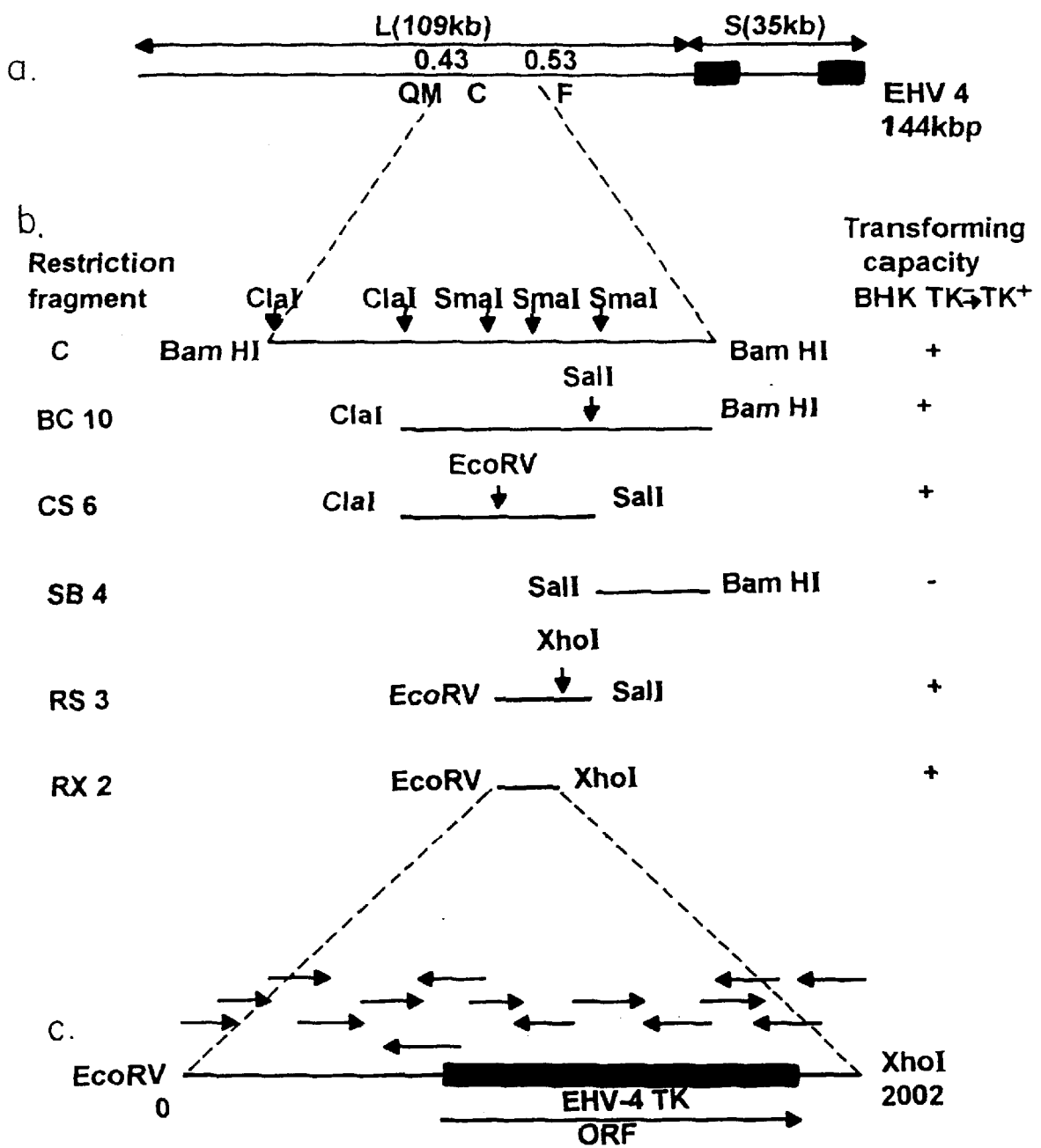
FIG. 1*a* is a schematic showing the localization of the TK gene on the Bam HI C fragment mapping between 0.43 and 0.53.

FIG. 1*b* is a schematic showing the testing of subfragments of EHV-4 BamHI C for the capacity to transform BHK TK- cells to TK+ phenotype, and the localization of TK-transforming activity to a 2 kbp EcoRV/XhoI fragment (RX2).

FIG. 1*c* is a schematic showing the subcloning of RX2 and the sequencing of overlapping fragments which resulted in the localization and nucleotide sequencing of the TK gene.

DETAILED DESCRIPTION OF THE INVENTION

It is an object of the present invention to provide an EHV-4 mutant which can be used for the preparation of a vaccine against EHV-4 infection, the mutant viruses being attenuated in a controlled way in a manner which excludes the reversion to virulence and which still elicit a strong immune response in host animals.

According to the present invention such a mutant EHV-4 is characterized in that it does not produce a functional thymidine kinase ($TK^-$) as a result of a deletion and/or insertion in the gene encoding thymidine kinase.

The development of techniques for controlled manipulation of genetic material has allowed the possibility of obtaining attenuated virus vaccines which avoid the disadvantages of the classic attenuated virus vaccines.

However, up to now no information was available with respect to the exact localisation on the EHV-4 genome of a region involved with the virulence of EHV-4 making the production of an genetic engineered attenuated EHV-4 impossible.

The gene encoding thymidine kinase was mapped within the BamHI C fragment of the EHV-4 genome and was further localised to an about 2 kbp EcoRV/XhoI fragment thereof, with a map position of approximately 0,48 (FIG. 1).

The nucleic acid sequence of the TK gene was determined and is shown in SEQ ID NO: 1 from which restriction enzyme cleavage sites to be used for the genetic manipulation of the gene can be derived.

The TK gene consists of 1056 nucleotides encoding a 352 amino acid enzyme of predicted molecular weight of 38.800 D. The efficiency of the expression of TK is regulated by the presence of expression control sequences. For example promoter sequences are involved in the binding of RNA polymerase to the DNA template and control the site and onset of the mRNA. Such sequences are often found within a 100 bp region before the transcription initiation site. Downstream transcriptional control signals are inter alia, the transcription termination codon and a polyadenylation signal. The TATA box positioned at base pair 21–25 is the putative promoter TATA box of the EHV-[4] TK gene. A potential RNA polymerase initiation site is located 22 bp downstream of the TATA box. A poly A signal is positioned 42 bp downstream of the termination codon (SEQ ID NO: 1).

It will be understood that for the DNA sequence of the EHV-4 TK gene natural variations can exist between individual EHV-4 viruses. These variations may result in a change of one or more nucleotides in the TK gene which, however still encodes a functional TK. Moreover, the potential exists to use genetic engineering technology to bring about above-mentioned variations resulting in a DNA sequence related to the sequence shown in SEQ ID NO: 1. It is clear that EHV-4 mutants comprising a deletion and/or insertion in such a related nucleic acid sequence are also included within the scope of the invention.

The EHV-4 deletion mutants of the present invention comprise a TK gene from which a DNA fragment has been deleted so that no functional TK enzyme is produced upon replication of the virus, e.g. as result of a change of the tertiary structure of the altered TK protein or as a result of a shift of the reading frame.

In addition the deletion in the genome of the EHV-4 mutant may comprise the complete TK gene.

EHV-4 mutants according to the invention can also be obtained by inserting a nucleic acid sequence into the TK coding region thereby preventing the expression of a functional TK enzyme. Such a nucleic acid sequence can inter alia be an oligonucleotide, for example of about 10–60 bp, preferably also containing one or more translational stop codons, or a gene encoding a polypeptide. Said nucleic acid sequence can be derived from any source, e.g. synthetic, viral, prokaryotic or eukaryotic.

In another embodiment of the present invention the EHV-4 deletion mutants can contain above-mentioned nucleic acid sequence in place of the deleted EHV-4 DNA.

It is another object of the present invention to provide a mutant EHV-4 which can be used not only for the preparation of a vaccine against EHV-4 infection but also against other equine infectious diseases. Such a vector vaccine based on a safe live attenuated EHV-4 mutant offers the possibility to immunize against other pathogens by the expression of antigens of said pathogens within infected cells of the immunized host and can be obtained by inserting a heterologous nucleic acid sequence encoding a polypeptide heterologous to EHV-4 in an insertion-region of the EHV-4 genome. However, the prerequisite for a useful EHV-4 vector is that the heterologous nucleic acid sequence is incorporated in a permissive position or region of the genomic EHV-4 sequence, i.e. a position or region which can be used for the incorporation of a heterologous sequence Without disrupting essential functions of EHV-4 such as those necessary for infection or replication. Such a region is called an insertion-region. Prior to the present invention no insertion-region in the EHV-4 genome has been described.

According to the present invention EHV-4 mutants are provided which can be used as a viral vector, characterized in that said mutants do not produce a functional TK as a result of an insertion of a heterologous nucleic acid sequence encoding a polypeptide an the gene encoding TK.

EHV-4 insertion mutants as described above having a heterologous nucleic acid sequence inserted in place of deleted TK DNA are also within the scope of the present invention.

The tern "EHV-4 insertion mutants" comprises inter alia infective viruses which have been genetically modified by the incorporation into the virus genome of a heterologous nucleic acid sequence, i.e. a gene which codes for a protein or part thereof said gene being different of a gene naturally present in EHV-4.

On infection of a cell by said EHV-4 insertion mutant it expresses the heterologous gene in the form of a heterologous polypeptide.

The term "polypeptide" refers to a molecular chain of amino acids with a biological activity, does not refer to a specific length of the product and if required can be modified in vivo or in vitro, for example by glycosylation, amidation, carboxylation or phosphorylation; thus inter alia peptides, oligopeptides and proteins are included within the definition of polypeptide.

The heterologous nucleic acid sequence to be incorporated into the EHV-4 genome according to the present invention can be derived from any source, e.g. viral, prokaryotic, eukaryotic or synthetic. Said nucleic acid sequence can be derived from a pathogen, preferably an equine pathogen, which after insertion into the EHV-4 genome can be applied to induce immunity against disease. Preferably, nucleic acid sequences derived from EHV-1, equine influenza virus, -rotavirus, -infectious anemia virus, arteritis virus, -encephalitis virus, Borna disease virus of horses, Berue virus of horses, *E. coli* or *Streptococcus equi* are contemplated of for incorporation into the insertion-region of the EHV-4 genome.

Furthermore, nucleic acid sequences encoding polypeptides for pharmaceutical or diagnostic application, in particular immune modulators such as lymphokines, interferons or cytokines, may be incorporated into said insertion-region.

An essential requirement for the expression of the heterologous nucleic acid sequence in a EHV-4 mutant is an adequate promoter operably linked to the heterologous nucleic acid sequence. It is obvious to those skilled in the art that the choice of a promoter extends to any eukaryotic, prokaryotic or viral promoter capable of directing gene transcription in cells infected by the EHV-4 mutant, such as the SV-40 promoter (Science 222, 524–527, 1983) or, e.g., the metallothionein promoter (Nature 296, 39–42, 1982) or a heat shock promoter (Voellmy et al., Proc. Natl. Acad. Sci. USA 82, 4949–53, 1985) or the human cytomegalovirus IE promoter or Promoters present in EHV-4, e.g. the TK promoter.

Well-known procedures for inserting DNA sequences into a cloning vector and in vivo homologous recombination can be used to introduce a deletion and/or an insertion into the EHV-4 genome (Maniatis, T. et al. (1982) in "Molecular cloning", Cold Spring Harbor Laboratory; European Patent Application 74.808; Roizman, B. and Jenkins, F. J. (1985), Science 229, 1208; Higuchi, R. et al. (1988), Nucleic Acids Res. 16, 7351). Briefly, this can be accomplished by constructing a recombinant DNA molecule for recombination with EHV-4 DNA. Such a recombinant DNA molecule may be derived from any suitable plasmid, cosmid, virus or phage, plasmids being most preferred, and contains EHV-4 DNA possibly having a nucleic acid sequence inserted therein if desired operably linked to a promoter. Examples of suitable cloning vectors are plasmid vectors such as pBR322, the various pUC and Bluescript plasmids, bacteriophages, e.g. λ gt-WES-λ B, charon 28 and the M13mp phages or viral vectors such as SV40, *Bovine papillomavirus*, Polyoma and Adeno viruses. Vectors to be used in the present invention are further outlined in the art, e.g. Rodriguez, R. L. and D. T. Denhardt, edit., Vectors: A survey of molecular cloning vectors and their uses, Butterworths, 1988.

First, an EHV-4 DNA fragment comprising the insertion region, i.e. the TK gene, is inserted into the cloning vector according to recDNA techniques. Said DNA fragment may comprise part of the TK gene or substantially the complete TK gene, and if desired flanking sequences thereof.

Second, if an EHV-4 TK deletion mutant is to be obtained at least part of TK gene is deleted from the recombinant DNA molecule obtained from the first step.

This can be achieved for example by appropriate exonuclease III digestion or restriction enzyme treatment of the recombinant DNA molecule from the first step.

In the case an EHV-4 insertion mutant is to be obtained the nucleic acid sequence is inserted into the TK gene present in the recombinant DNA molecule of the first step or in place of the TK DNA deleted from said recombinant DNA molecule. The EHV-4 DNA sequences which flank the deleted TK DNA or the inserted nucleic acid sequence should be of appropriate length as to allow homologous recombination with the viral EHV-4 genome to occur.

If desired, a construct can be made which contains two or more different inserted (heterologous) nucleic acid sequences derived from e.g. the same or different pathogens said sequences being flanked by insertion-region sequences of EHV-4 defined herein. Such a recombinant DNA molecule can be employed to produce an EHV-4 mutant which expresses two or more different antigenic polypeptides to provide a multivalent vaccine.

Thereafter, cells, for example rabbit cells, $TK^+$ or $TK^-$ phenotype, or equine cells, e.g. equine dermal cells, can be transfected with EHV-4 DNA in the presence of the recombinant DNA molecule containing the deletion and/or insertion of (heterologous) nucleic acid sequence flanked by appropriate EHV-4 sequences whereby recombination occurs between the corresponding regions in the recombinant DNA molecule and the EHV-4 genome. Recombination can also be brought about by transfecting EHV-4 genomic DNA containing host cells with a DNA containing the (heterologous) nucleic acid sequence flanked by appropriate flanking insertion-region sequences without vector DNA sequences. Recombinant viral progeny is thereafter produced in cell culture and can be selected for example genotypically or phenotypically, e.g. by hybridization, detecting enzyme activity encoded by a gene co-integrated along with the (heterologous) nucleic acid sequence, screening for EHV-4 mutants which do not produce functional TK (Roizman, B. and Jenkins, F. J. (1985), ibid)) or detecting the antigenic heterologous polypeptide expressed by the EHV-4 mutant immunologically. The selected EHV-4 mutant can be cultured on a large scale in cell culture whereafter EHV-4 mutant containing material or heterologous polypeptides expressed by said EHV-4 can be collected therefrom. Alternatively, mutant EHV-4 could be generated by cotransfection of several cosmids, containing between them the entire EHV-4 genome, where an insertion and/or deletion has been engineered into the cosmid possessing EHV-4 TK DNA.

According to the present invention a live attenuated EHV-4 mutant which does not produce a functional TK, and if desired expresses one or more different heterologous polypeptides of specific pathogens can be used to vaccinate horses, susceptible to EHV-4 and these pathogens.

Vaccination with such a live vaccine is preferably followed by replication of the EHV-4 mutant within the inoculated host, expressing in vivo EHV-4 polypeptides, and if desired heterologous polypeptides. An immune response will subsequently be elicited against EHV-4 and the heterologous polypeptides. An animal vaccinated with such an EHV-4 mutant will be immune for a certain period to subsequent infection of EHV-4 and above-mentioned pathogen(s).

An EHV-4 mutant according to the invention optionally containing and expressing one or more different heterologous polypeptides can serve as a monovalent or multivalent vaccine.

An EHV-4 mutant according to the invention can also be used to prepare an inactivated vaccine.

For administration to animals, the EHV-4 mutant according to the presentation can be given inter alia by aerosol, spray, drinking water, orally, intradermally, subcutaneously or intramuscularly. Ingredients such as skimmed milk or glycerol can be used to stabilise the virus. It is preferred to vaccinate horses by intranasal administration. A dose of $10^3$ to $10^8$ $TCID_{50}$ of the EHV-4 mutant per horse is recommended in general.

It is a further object of the present invention to produce subunit vaccines, pharmaceutical and diagnostic preparations comprising a heterologous polypeptide expressed by an EHV-4 mutant according to the invention. This can be achieved by culturing cells infected with said EHV-4 mutant under conditions that promote expression of the heterologous polypeptide. The heterologous polypeptide may then be purified with conventional techniques to a certain extent depending on its intended use and processed further into a preparation with immunizing therapeutic or diagnostic activity.

The above described active immunization against specific pathogens will be applied as a protective treatment in healthy animals. It goes without saying that animals already infected with a specific pathogen can be treated with antiserum comprising antibodies evoked by an EHV-4 mutant according to the invention. Antiserum directed against an EHV-4 mutant according to the invention can be prepared by immunizing animals with an effective amount of said EHV-4 mutant in order to elicit an appropriate immune response. Thereafter the animals are bled and antiserum can be prepared.

EXAMPLE 1

Isolation and Characterization of EHV-4 Insertion Region

1. Culturing of EHV-4 Virus

Roller bottles of slightly sub-confluent monolayers of equine dermal cells (NBL-6) grown in Earle's Minimum Essential Medium (Flow) supplemented with 0,2% sodium bicarbonate, 1% non-essential amino acids, 1% glutamine, 100 units/ml penicillin, 100 mg/ml streptomycin and 10% foetal calf serum were infected with virus of the EHV-4 strain 1942 at a m.o.i. of 0,003 and allowed to adsorb for 60 min at 37° C. They were incubated at 31° C. until extensive c.p.e. was evident and the majority of cells had detached from the bottle surface (2–6 days). The infected cell medium was centrifuged at 5.000 r.p.m. for 5 min to pellet the cells, and the supernatant was centrifuged at 12.000 r.p.m. for 2 hours in a Sorvall GSA 6×200 ml rotor. The pellet was resuspended in 5 ml PBS, sonicated and centrifuged at 11.000 r.p.m. in a Sorvall SS34 rotor for 5 min to spin down cellular debris. Virus was then pelleted by centrifugation at 18.000 r.p.m. in a Sorvall SS34 rotor for 1 hour. Ratios of virus particles to plaque-forming units were approximately 1.000 to 5.000.

2.Preparation of EHV-4 DNA

The pelleted virus was resuspended in 10 ml NTE (NaCl/Tris/EDTA) and briefly sonicated. Contaminating cellular DNA was degraded by adding DNase at 10 µg/ml and incubating at 37° C. for 1 hour. SDS was added to a final concentration of 2%, and the preparation was extracted approximately 3 times with NTE equilibrated phenol until a clear interphase was obtained.

A chloroform extraction was followed by ethanol precipitation of the DNA as described above. The DNA was pelleted, washed with 70% ethanol, resuspended in 10 ml of 100 mM NaCl and 10 4g/ml RNase and left overnight at room temperature. Further purification was achieved by treatment with 1 mg/ml proteinase K for 2 hours at 31° C. The DNA was extracted once with phenol:chloroform (1:1 vol/vol), once with chloroform, ethanol precipitated, drained well and resuspended in 0.1×SSC.

3. Cloning of EHV-4 DNA

EHV-4 BamHI DNA fragments were ligated into the vector pUC9, a plasmid which includes the ampicillin-resistance gene from pBR322 and the polylinker region from M13mp9 (Vieira, J. and Messing, J. (1982), Gene 19, 259). 5 μg of EHV-4 DNA and 5 μg pUC9 DNA were separately digested with BamHI.

Complete digestion was verified by gel electrophoresis of aliquots of the reactions and then the DNA was extracted twice with an equal volume of phenol:chloroform (1:1) and ethanol-precipitated. Ligation was performed essentially by the method of Tanaka and Weisblum (J. Bact. 121, 354, 1975). Approximately 0.1 μg of BamHI digested pUC9 and 1 μg of BamHI-digested EHV-4 DNA were mixed in 50 mM Tris-HCl pH 7,5, 8 mM $MgCl_2$, 10 mM dithiothreitol, 1 mM ATP in a final volume of 40 μl. 2 units of T4 DNA ligase (0,5 μl) were then added. The reaction was incubated at 4° C. for 16 hours.

Calcium-shocked *E. coli* DHI cells (Hanahan, D. (1983), J. Mol. Biol. 166, 557) were transformed with the recombinant plasmids essentially described by Cohen et al. (Proc. Natl. Acad. Sci., USA 69, 2110, 1972). Additional clones were derived by restriction digestion of recombinant plasmid pUC9 containing BamHI C fragment FIG. 1*b*), followed by recovering of the specific EHV-4 restriction fragments and sub-cloning thereof within the multi-cloning site of the Bluescript M13+ plasmid vector (Stratagene; Maniatis, T. et al. ibid). 20 μg of each construct was transfected into monolayer BHK TK⁻ cells by a modification of the technique of Graham and van der Eb (Virology 52, 456, 1973; CellPhect Transfection Kit, according to manufactures instructions) TK+ colonies were selected in HAT supplemented medium (Hypoxanthine $10^{-4}$ M, Aminopterin $4×10^{-5}$ M, thymidine $1,6×10^5$ M).

TK transforming activity was thus localised to a 2 kbp EcoRV/XhoI fragment (RX2), cloned in construct pBSRX2, with a map position of approximately 0,48 (FIG. 1*b*).

The nucleotide sequence of both strands of fragment RX2 was determined by using single stranded plasmid DNA as template and Bluescript-derived custom-made oligonucleotides as primers in a Sanger dideoxy sequencing strategy (Sanger et al., Proc. Natl. Acad. Sci: 74, 5463, 1977) (FIG. 1*c*). The exact localisation, nucleic acid sequence and corresponding amino acid sequence of the TK gene is shown in the SEQ ID NO: 1 and SEQ ID NO: 2.

EXAMPLE 2

Preparation of TK-Deleted Plasmids

Restriction mapping and sequence analysis of DNA spanning the EHV-4 TK gene indicated that unique SmaI and BstXI sites exist within fragment RS3 (FIG. 1, 2) and unique SmaI and BstEII sites exist within RX2, all of which map within the TK coding region. A 0,73 kbp deletion within the TK gene was achieved by cloning RS3 into pUC 8 (at the SmaI and SalI sites within the multicloning site) and digesting the contruct with SmaI and BstXI. The vector fragment plus EHV-4 DNA flanking the deletion was isolated and the overhang generated by BstXI filled in using T4 pol. The linear plasmid was then self ligated to produce a plasmid containing RS3 fragment deleted from the SmaI-BstXI site (FIG. 2*b*). A 0,52 kbp deletion within the TK gene was achieved by cloning EHV-4 RX2 into a Bluescript vector (at the SmaI and XhoI sites within the multicloning site) and deleting from the SmaI-BstEII sites within the TK gene by restriction digestion with these enzymes. The larger vector fragment was separated from the 0,52 kbp EHV-4 fragment, the overhang filled in and the plasmid religated. The resultant plasmid possesses the 5' and 3' coding regions of the EHV-4 TK gene but is deleted from the SmaI-BstEII sites (FIG. 2*c*).

EXAMPLE 3

Use of Recombinant PCR to Produce TK-Constructs

The two plasmid constructs preferred in Example 2 contain EHV-4 DNA with distinct deletions within the TK gene. The positions of these deletions are dictated by the availability of restriction endonuclease sites within the TK gene which could be utilised in the deletion strategy. Both deletions span the N-terminal coding region of the TK gene. Given that this region is likely to contain the promoter for the adjacent UL24-type gene, incorporation of these DNAs into the EHV genome could possibly result in the altered expression of both the UL24-type gene and of the TK gene. DNAs were therefore constructed with deletions within the C-terminal coding region of the TK gene in order to ultimately produce EHV recombinants affected solely in TK expression. Recombinant polymerase chain reaction (PCR) was utilised to prepare these DNAs since, this technique permits the deletion to be localised anywhere within the gene. As shown in FIGS. 2 and 3 we synthesised two primer sets (primers 1,2 and 3,4) which were utilised independently to prepare DNA fragments mapping to the left and right of the deletion site (step 1). The external primers (primers 1,4) were then utilised to amplify across the products of the first round PCR reactions (primers 2,3 having complementary annealable end regions) to produce the TK-construct (steps 2,3). Such a strategy has the added advantage that restriction endonuclease sites can be inserted at the termini and at the deletion site by incorporation within the primers. These sites can be utilised to facilitate cloning of the TK- DNA PCR product into a suitable plasmid vector (step 4) and to effect cloning within the deletion site.

Primers

The 3' terminal sequences of the following primers were derived from the published sequence information on the TK genes of EHV-1 and EHV-4 (sequences underlined below). 5' sequences incorporating a 'GC' clamp (to enhance the efficiency of cleavage with intra-primer restriction enzymes), and 3 restriction enzyme sites. In the case of primers 2 and 3 the 5' regions of the primers are complementary in order to facilitate annealing of denatured first round amplification products at step 2.

LMU (Primer 1) (SEQ ID NO:3)
5'-GCGGATCGATAGATCTGCGGCCGC<u>TGCGTTAGTGGTGTT</u>-3'
ClaI BglII NotI LIL (Primer 2) (SEQ ID NO:4)
5'-GAGCTCGATATCTCTAGA<u>GTAGGGCGTGGTAAAGC</u>-3'
SstI EcoRV XbaI RIU (Primer 3) (SEQ ID NO:5)
5'-TCTAGAGATATCGAGCTC<u>ATATTGGAAGTTCACGC</u>-3'
XbaI EcoRV SstI RML (Primer 4) (SEQ ID NO:6)

```
                         -continued
5'-CCGGGATCCAGATCTGCGGCCGCTCAGAAGATGTGTACGA-3'
      BamHI BglII  NotI
```

The PCR technique is carried out as follows. First primers 1 and 2 are hybridized onto the single stranded EHV genome. Then the second strand is extended along the first strand starting from primer 1 using a DNA polymerase until the primer 2 is encountered, when DNA synthesis stops. Similarly a second DNA oligonucleotide strand is synthesised from primer 3 up to primer 4. The strands are then dehybridised into single DNA strands by heating. If necessary the process can be repeated using further quantities of primer in order to amplify the amount of PCR product.

Legends

Figure 2:
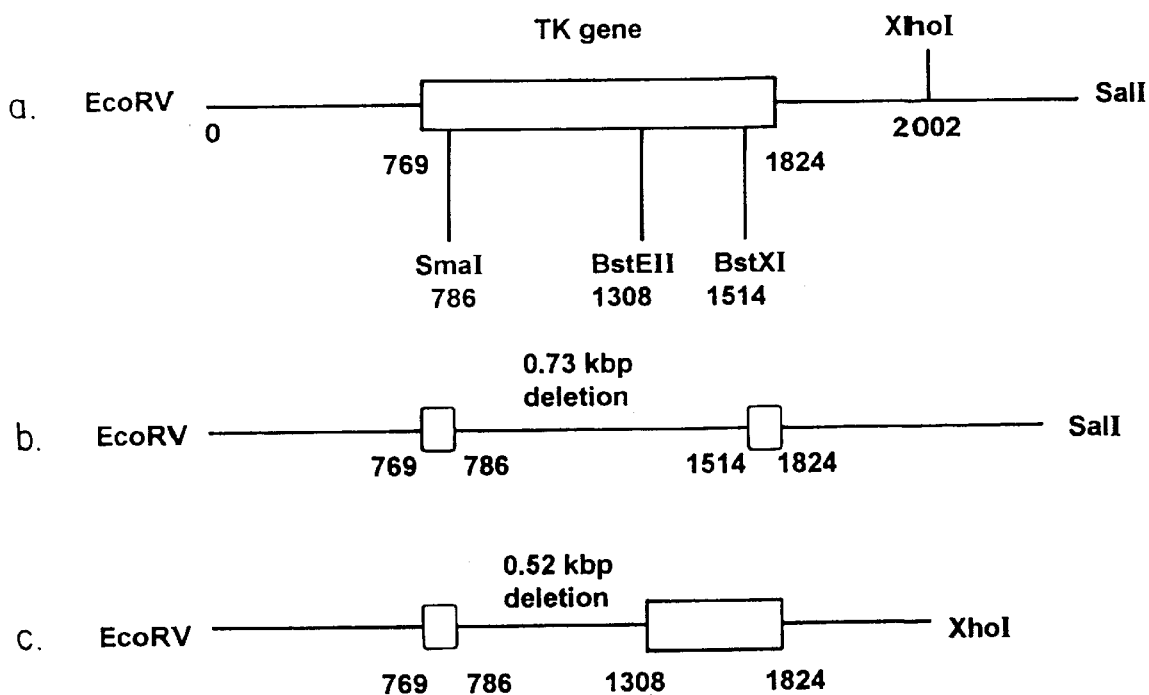
FIG. 2*a* is a schematic showing the restriction enzyme pattern of fragment RS3 containing TK gene.


FIG. 2*b* is a schematic showing a 0.73 kbp deletion in TK gene (SmaI-BstXI) deleted from RS3.

FIG. 2*c* is a schematic showing a 0.52 kbp deletion in TK gene (SmaI-BstEII) deleted from RX2.

FIG. 1. Strategy for the localisation and sequencing of the EHV-4 thymidine kinase gene.
(a) the TK gene was localised on the BamHI C fragment mapping between 0,43 and 0,53.
(b) subfragments of EHV-4 BamHI C were tested for their capacity to biochemically transfrom BHK TK⁻ cells to TK⁺ phenotype. TK⁻ transforming activity was localised to a 2 kbp EcoRV/XhoI fragment, RX2.
(c) subcloning of RX2 and sequencing of overlapping fragments resulted in the exact localisation and nucleotide sequence of the TK gene.

FIG. 2.
(a) Restriction enzyme pattern of fragment RS3 containing TK gene.
(b) 0,73 kbp deletion in TK gene (SmaI-BstXI) deleted from RS3.
(c) 0,52 kbp deletion in TK gene (SmaI-BstEII) deleted from RX2.

Figure 3:
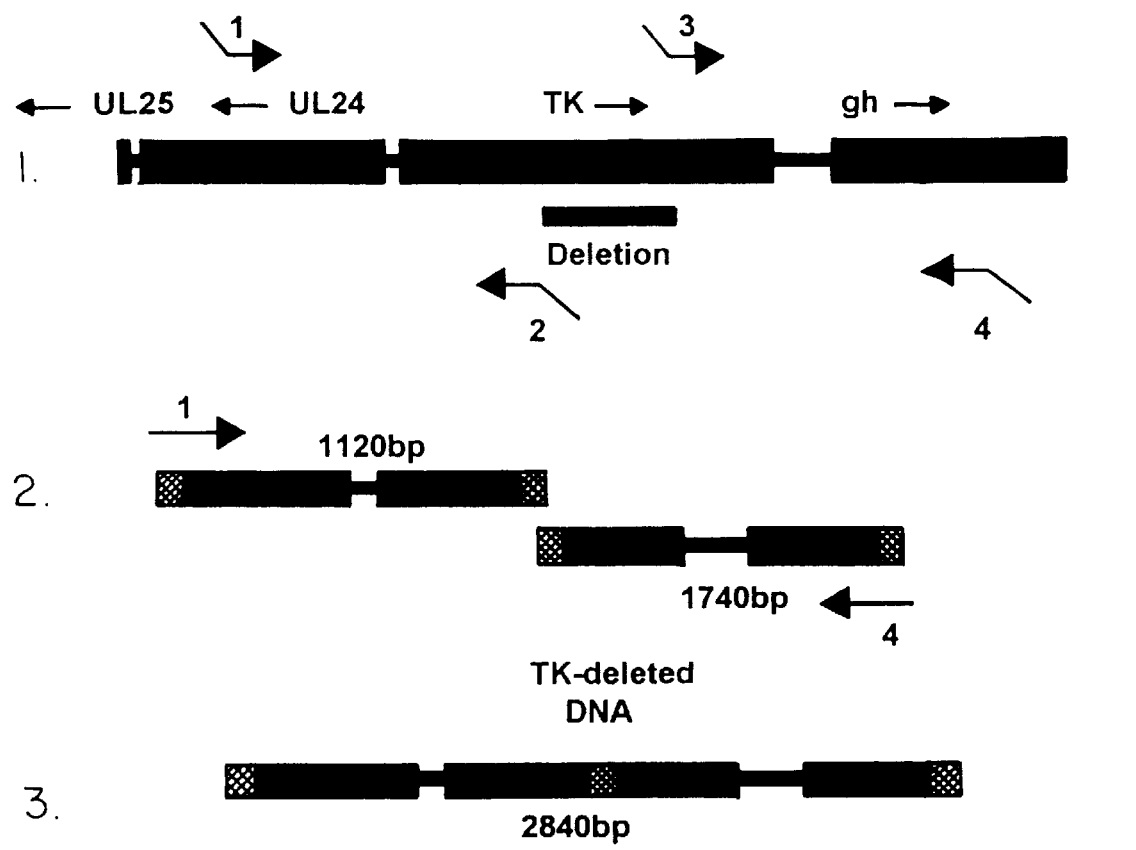
FIG. 3 is a schematic showing the strategy used to delete a region of the TK gene using a polymerase chain reaction (PCR) technique according to steps 1–3 of Example 4.
Figure 4:
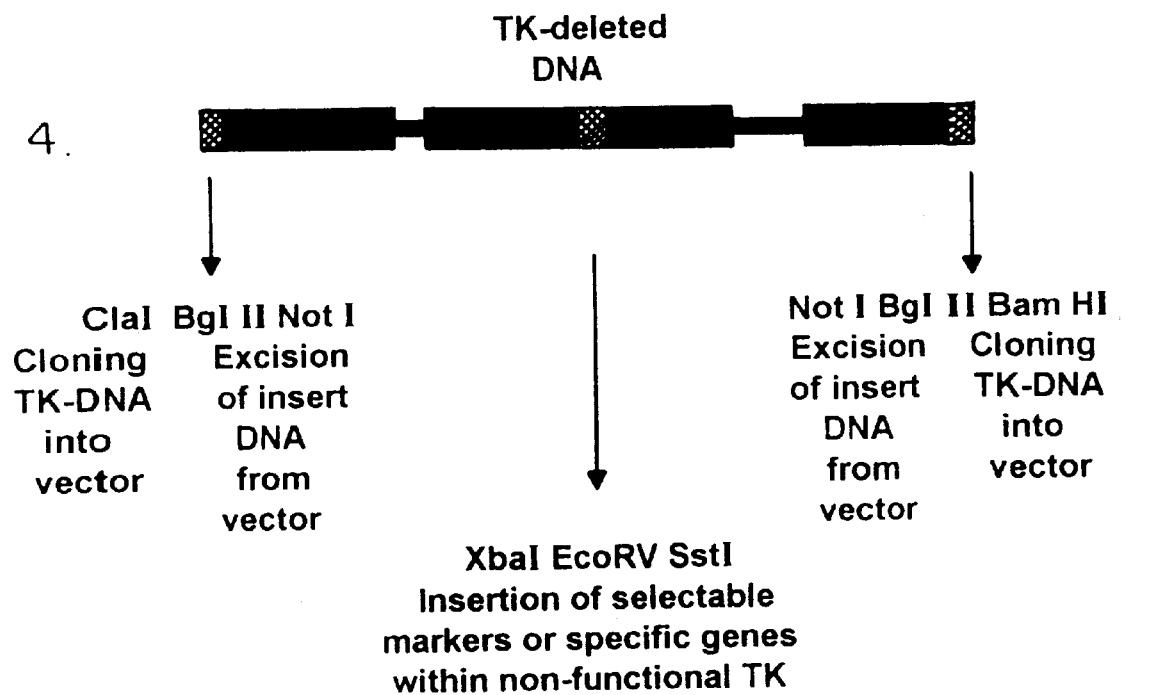
FIG. 4 is a schematic showing the strategy for cloning the TK-DNA PCR product obtained from Example 4 into a suitable plasmid vector.

FIG. 3. shows the strategy for deletion of a region of the TK gene using a polymerase chain reaction (PCR) technique according to steps 1 to 3 of Example 4; and FIG. 4. shows the strategy for cloning of the TK- DNA PCR product obtained from Example 4 into a suitable plasmid vector (step 4).

That which is claimed is:

1. An EHV-4 mutant characterized in that it does not produce a functional thymidine kinase as a result of a deletion and/or insertion in the gene encoding thymidine kinase, the deletion and/or insertion being made at a position within the thymidine kinase gene so as to not alter expression of the UL24 gene such that virus replication is not disrupted; wherein the deletion or insertion is in the C-terminal coding region of the thymidine kinase gene.

2. An EHV-4 mutant according to claim 1, characterized in that at least one heterologous nucleic acid sequence encoding a polypeptide is inserted.

3. An EHV-4 mutant according to claim 2 characterized in that the heterologous nucleic acid sequence is under control of a promoter regulating the expression of said nucleic acid sequence in a cell infected with said EHV-4 mutant.

4. An EHV-4 mutant according to claim 2 characterized in that the heterologous nucleic acid sequence encodes an antigen of an equine pathogen.

5. An EHV-4 mutant according to claim 4 characterized in that the antigen is an EHV-1, or equine influenza antigen.

6. An EHV-4 mutant characterized in that it does not produce a functional thymidine kinase as a result of a deletion and/or insertion in the gene encoding thymidine kinase, the deletion and/or insertion being made at a position within the thymidine kinase gene so as to not alter expression of the UL24 gene such that virus replication is not disrupted; wherein the thymidine kinase gene prior to said deletion and/or insertion has a sequence according to SEQ ID NO:1.

7. An EHV-4 mutant, characterized in that it does not produce a functional thymidine kinase as a result of a deletion and/or insertion in the gene encoding thymidine kinase, the deletion and/or insertion being made at a position within the thymidine kinase gene such that virus replication is not disrupted; wherein the deletion or insertion is in the C-terminal coding region of the thymidine kinase gene.

8. An EHV-4 mutant according to claim 7 characterized in that at least one heterologous nucleic acid sequence encoding a polypeptide is inserted.

9. An EHV-4 mutant according to claim 8 characterized in that the heterologous nucleic acid sequence is under control of a promoter regulating the expression of said nucleic acid sequence in a cell infected with said EHV-4 mutant.

10. An EHV-4 mutant according to claim 8 characterized in that the heterologous nucleic acid sequence encodes an antigen of an equine pathogen.

11. An EHV-4 mutant according to claim 10 characterized in that the antigen is an EHV-1, or equine influenze antigen.

12. Cell culture infected with an EHV-4 mutant according to claim 7.

13. A recombinant DNA molecule comprising a vector molecule and a EHV-4 thymidine kinase gene which has a deletion and/or insertion in the C-terminal coding region of the thymidine kinase gene; said recombinant DNA molecule being able to homologously recombine with the viral EHV-4 genome to produce a mutant EHV-4 according to claim 7.

14. Host cell containing a recombinant DNA molecule according to claim 13.

15. A process for the preparation of an EHV-4 mutant which does not produce a functional thymidine kinase as a result of a deletion and/or insertion in the C-terminal coding region of the thymidine kinase gene, the deletion and/or insertion being made at a position such that virus replication is not disrupted, comprising co-transfection of a cell culture with EHV-4 DNA and a recombinant DNA molecule according to claim 13.

* * * * *

UNITED STATES PATENT AND TRADEMARK OFFICE
CERTIFICATE OF CORRECTION

PATENT NO. : 6,025,181

DATED : February 15, 2000

INVENTOR(S) : Onions et al.

It is certified that error appears in the above-identified patent and that said Letters Patent is hereby corrected as shown below:

Title page, [56] References Cited:

U.S. PATENT DOCUMENTS, line 2, "Sheddert" should read --Studdert--; line 4, "Rey-Snelonge et al." should read --Rey-Senelonge et al.--.

Signed and Sealed this

Nineteenth Day of December, 2000

Attest:

Q. TODD DICKINSON

*Attesting Officer*           *Commissioner of Patents and Trademarks*